United States Patent [19]
Animati et al.

[11] Patent Number: 5,814,608
[45] Date of Patent: Sep. 29, 1998

[54] S-FLUORO-ANTHRACYCLINES, PROCESSES FOR THEIR PREPARATION AND PHARMACEUTICAL COMPOSITIONS CONTAINING THEM

[75] Inventors: Fabio Animati, Rome; Federico Arcamone, Nerviano; Giuseppe Giannini, Turi; Paolo Lombardi, Cesate; Edith Monteagudo, Pomezia, all of Italy

[73] Assignees: Bristol-Myers Squibb, S.p.A., Sermoneta; A. Menarini Industrie Farmaceutiche Riunite S.R.L., Florence, both of Italy

[21] Appl. No.: 776,627

[22] PCT Filed: Aug. 1, 1995

[86] PCT No.: PCT/EP95/03061

§ 371 Date: Apr. 21, 1997

§ 102(e) Date: Apr. 21, 1997

[87] PCT Pub. No.: WO96/04292

PCT Pub. Date: Feb. 15, 1996

(Under 37 CFR 1.47)

[30] Foreign Application Priority Data

Aug. 4, 1994 [IT] Italy .................................. MI9A01696

[51] Int. Cl.$^6$ ......................... C07H 15/252; A61K 31/70; C07D 309/06; C07C 49/747
[52] U.S. Cl. ............................. 514/34; 536/6.4; 549/419; 552/201
[58] Field of Search ............................. 552/201; 536/6.4; 514/34; 549/419

[56] References Cited

FOREIGN PATENT DOCUMENTS

| 0 436 474 | 7/1991 | European Pat. Off. . |
| 0 457 215 | 11/1991 | European Pat. Off. . |
| 91/19725 | 12/1991 | WIPO . |
| 95/09173 | 4/1995 | WIPO . |

OTHER PUBLICATIONS

De Mesmaeker, Alain, et al., "A New Protected Form of Glucuronic Acid for the Synthesis of Labile 1–o–Acyl–β–D–Glucurionides," *Tetrahedron Letters*, vol. 30, No. 29, pp. 3773–3776, 1989.

Arcamone, F. *Doxorubicin: Anticancer Antibiotics*. Medicinal Chemistry Series, vol. 17, Academic press, 1981. (entire book, not supplied).

Corey, E. J., "Cleavage of Allyloxycarbonyl Protecting Group from Oxygen and Nitrogen Under Mild Conditions by Nickel Carbonyl," *J. Org. Chem.*, vol. 33, No. 18, pp. 3223–3224, 1973.

Albanese, Domenico, et al. "Tetrabutylammonium Dihydrogentrifluoride: An Effective Source of Fluoride Ion For Halofluorination of Alkenes," *Gazzette Chimica Italiana*, 121, pp. 537–541, 1991.

Lal. G. Sankar. "Site–Selective Fluorination of Organic Compounds Using 1–Alkyl–4–fluoro–1, 4–diazabicycol [2.2.2]octane Salts (Selectfluor Reagents), " *J. Org. Chem.*, vol. 58, pp. 2791–2796, 1993.

Wong, C.M., et al, "Synthetic Studies of Hydronaphthacenic Antibiotics. I. The Synthesis of 4–Demethoxy–7–O–menthyl Daunomycinone," Department of Chemistry, University of Manitoba, Mar. 23, 1971, (7 pages).

Smith, Thomas H., et al, "Synthetic Approaches to Adriamycin, Degradation of Daunorubicin to Nonasymmetric Tetracyclic Ketone and Refunctionalization of the A–Ring to Adriamycin," *Journal of the American Chemical Society*, Mar. 31, 1976, pp. 1969–1971.

Kende, Andrew S., et al, "Total Synthesis of (±)–Duanomycinone and (±)–Carminomycinone," *Journal of the American Chemical Society*, Mar. 31, 1976, pp. 1967–1969.

Giolitti et al., Tetrahedron Letters, vol. 33,No. 12,pp. 1637–1640, 17 Mar. 1992.

Canfarini et al.,Tetrahedron Letters,vol. 34,No. 29,pp. 4697–4700, 16 Jul. 1993.

Chemical Abstracts,vol. 117,No.3,abst.no.27,045q,Jul. 20, 1992.

*Primary Examiner*—Alan L. Rotman
*Attorney, Agent, or Firm*—McDermott, Will & Emery

[57] ABSTRACT

8-fluoro-anthracyclines of formula (I) have anti-tumor activity.

wherein:
R is chosen in the group consisting of H, OH, OR$_4$ wherein R$_4$ is chosen in the group consisting of CHO, COCH$_3$, acyl derivative of a carboxylic acid containing up to 6 carbon atoms;
R$_1$ is chosen in the group consisting of: H, OH, OCH$_3$;
R$_2$ is chosen in the group consisting of: H, OH, NH$_2$
R$_3$ is chosen in the group consisting of: H, OH, NH$_2$, residue of formula (A)

The compounds are characterized by having cis-stereochemistry between the groups 8—F and 9—OH. Their preparation and pharmaceutical compositions containing them are also described.

6 Claims, No Drawings

S-FLUORO-ANTHRACYCLINES, PROCESSES FOR THEIR PREPARATION AND PHARMACEUTICAL COMPOSITIONS CONTAINING THEM

FIELD OF THE INVENTION

Glycosidic derivatives of 8-fluoro-anthracyclinone of general formula (I) are described:

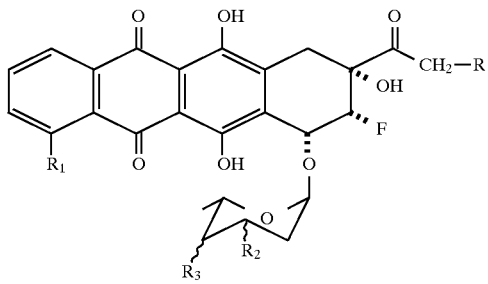

wherein:
R is chosen in the group consisting of H, OH, $OR_4$ wherein $R_4$ is chosen in the group consisting of CHO, COCH acyl derivative of a carboxylic acid containing up to 6 carbon atoms;
$R_1$ is chosen in the group consisting of: H, OH, $OCH_3$;
$R_2$ is chosen in the group consisting of: H, OH, $NH_2$
$R_3$ is chosen in the group consisting of: H, OH, $NH_2$, residue of formula (A)

wherein $R_5$ and $R_6$, same or different, are chosen in the group consisting of: H, OH, $NH_2$ and the symbol ($\sim$) indicates that the substituents $R_2$, $R_3$, $R_5$ and $R_6$ can be in the axial or equatorial configuration; and wherein the groups 8—F and 9—OH are in position cis; their pharmaceutically acceptable salts, procesess for their preparation and pharmaceutical compositions containing them.

STATE OF THE ART

Daunorubicin (daunomicin) and 4-demethoxydaunorubicin (idarubicin), and their derivatives containing an hydroxylated lateral chain (doxorubicin), are glycosides presenting well-known anti-tumoral properties; their preparation and use were already described (F. Arcamone "Doxorubicin: Anticancer Antibiotics" Medicinal Chemistry Series Vol. 17, Academic press 1981).

The 8-fluoro-anthracyclines are a class of anthracyclines already known (see for example: EP-A-0436474; EP-A-0457215; WO 95/09173) for their higher activity and selectivity in respect of the corresponding non-fluorinated compounds.

It has been surprisingly found, and this is an object of the present application, that when the two substituents 8—F and 9—OH have cis-stereochemistry, the corresponding derivatives are surprisingly more active, especially in respect of tumoral cells resistant against the already known compounds.

DETAILED DESCRIPTION OF THE INVENTION

The present invention refers to glycosidic derivatives of 8-fluoroanthracylinone of general formula

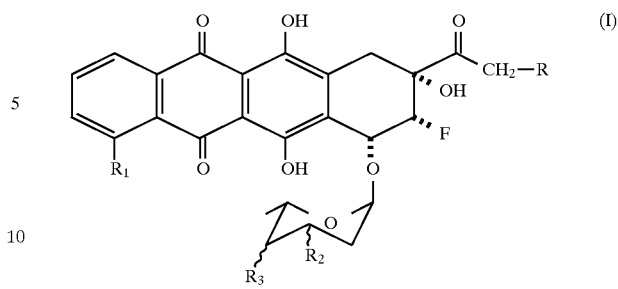

wherein:
R is chosen in the group consisting of H, OH, $OR_4$ wherein $R_4$ is chosen in the group consisting of CHO, $COCH_3$, acyl derivative of a carboxylic acid containing up to 6 carbon atoms;
$R_1$ is chosen in the group consisting of: H, OH, $OCH_3$;
$R_2$ is chosen in the group consisting of: H, OH, $NH_2$
$R_3$ is chosen in the group consisting of: H, OH, $NH_2$, residue of formula (A)

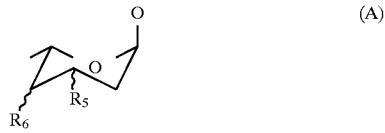

wherein $R_5$ and $R_6$, same or different, are chosen in the group consisting of: H, OH, $NH_2$ and the symbol ($\sim$) indicates that the substituents $R_2$, $R_3$, $R_5$ and $R_6$ can be in the axial or equatorial configuration; and wherein the groups 8—F and 9—OH are in position cis; their pharmaceutically acceptable salts, process for their preparation and pharmaceutical compositions containing them.

More particularly the present invention refers to the following compounds:
1) 4-demethoxy-8-(R)-fluoro-daunorubicin (I: R=$R_1$=H; $R_2$=$NH_2$; $R_3$=OH)
2) 4-demethoxy-8-(R)-fluoro-3'-deamino-4'deoxy-4'amino-daunorubicin (I: R=$R_1$=$R_2$=H; $R_3$=$NH_2$)
3) 4-demethoxy-8-(R)-fluoro-3'-deamino-4'deoxy-4'-epi-amino-daunorubicin (I: R=$R_1$=$R_2$=H; $R_3$=$NH_2$)
4) 4-demethoxy-8-(R)-fluoro-4'epi-daunorubicin (I: R=$R_1$=H; $R_2$=$NH_2$; $R_3$=OH)
5) 4-demethoxy-8-(R)-fluoro-7-(daunosaminyl-fucosyl)-daunorubicinone (I: R=$R_1$=H; $R_3$=A; $R_2$=$R_6$=OH; $R_5$=$NH_2$)
6) 4-demethoxy-8-(R)-fluoro-7-(daunosaminyl-ramnosyl)-daunorubicinone (I: R=$R_1$H; $R_3$=A; $R_2$=$R_6$=OH; $R_5$=$NH_2$)
7) 4-demethoxy-8-(R)-fluoro-7-(2",3",4"-trideoxy-4"-amino-esapiranosyl-fucosyl)-daunorubicinone (I: R=$R_1$=$R_5$=H; $R_3$=A; $R_2$=OH; $R_6$=$NH_2$)
8) 4-demethoxy-8-(R)-fluoro-7-(2",3",4"-trideoxy-4"-amino-esapiranosyl-ramnosyl)-daunorubicinone (I: R=$R_1$=$R_5$=H; $R_3$=A; $R_2$=OH; $R_6$=$NH_2$)
9) 4-demethoxy-8-(R)-fluoro-7-(fucosyl-4'-O-fucosyl)-daunorubicinone (I: R=$R_1$=H; $R_3$=A; $R_2$=$R_5$=$R_6$=OH)
10) 4-demethoxy-8-(R)-fluoro-7-fucosyl-4'-O-ramnosyl)-daunorubicinone (I: R=$R_1$=H; $R_3$ A; $R_2$=$R_5$=$R_6$=OH)
11) 8-(R)-fluoro-daunorubicin (I: R=H; $R_1$=$OCH_3$; $R_2$=$NH_2$; $R_3$=OH)
12) 8-(R)-fluoro-3'-deamino-4'deoxy-4'amino-daunorubicin (I: R=$R_2$=H; $R_1$=$OCH_3$; $R_3$=$NH_2$)
13) 8-(R)-fluoro-3'-deamino-4'deoxy-4'-epi-amino-daunorubicin (I: R=$R_2$=H; $R_1$=$OCH_3$; $R_3$=$NH_2$)

14) 8-(R)-fluoro-4'epi-daunorubicin (I: R=H; $R_1$=OCH$_3$; $R_2$=NH$_2$; $R_3$=OH)
15) 8-(R)-fluoro-7-(daunosaminyl-fucosyl)-daunorubicinone (I: R=H; $R_1$=OCH$_3$; $R_3$=A; $R_2$=$R_6$=OH; $R_5$=NH$_2$)
16) 8-(R)-fluoro-7-(daunosaminyl-ramnosyl)-daunorubicinone (I: R=H; $R_1$=OCH$_3$; $R_3$=A; $R_2$=$R_6$=OH; $R_5$=NH$_2$)
17) 8-(R)-fluoro-7-(2",3",4"-trideoxy-4"-amino-esapiranosyl-fucosyl)-daunorubicinone (I: R=$R_5$=H; $R_1$=OCH$_3$; $R_3$=A; $R_2$=OH; $R_6$=NH$_2$)
18) 8-(R)-fluoro-7-(2",3",4"-trideoxy-4"-amino-esapiranosyl-ramnosyl)-daunorubicinone (I: R=$R_5$=H; $R_1$=OCH$_3$; $R_3$=A; $R_2$=OH; $R_6$=NH$_2$)
19) 8-(R)-fluoro-7-(fucosyl-4'-O-fucosyl)-daunorubicinone (I: R=H; $R_1$=OCH$_3$; $R_3$=A; $R_2$=$R_5$=$R_6$ OH)
20) 8-(R)-fluoro-7-fucosyl-4'-O-ramnosyl)-daunorubicinone (I: R H; $R_1$=OCH$_3$; $R_3$=A; $R_2$=$R_5$=$R_6$=OH)
21) 4-demethoxy-8-(R)-fluoro-doxorubicin and its esters in C—14 (I: R=$R_3$=OH; $R_1$=H; $R_2$=NH$_2$)
22) 4-demethoxy-8-(R)-fluoro-3'-deamino-4'deoxy-4'amino-doxorubicin and its esters in C—14 (I: R=OH; $R_1$=$R_2$=H; $R_3$=NH$_2$)
23) 4-demethoxy-8-(R)-fluoro-3'-deamino-4'deoxy-4'-epi-amino-doxorubicin and its esters in C—14 (I: R=OH; $R_1$=$R_2$=H; $R_3$=NH$_2$)
24) 4-demethoxy-8-(R)-fluoro-4'epi-doxorubicin and its esters in C—14 (I: R=R OH; $R_1$=H; $R_2$ NH$_2$)
25) 4-demethoxy-8-(R)-fluoro-7-(daunosaminyl-fucosyl)-doxorubicinone and its esters in C—14 (I: R=$R_2$=$R_6$=OH; $R_3$=A; $R_1$=H; $R_5$=NH$_2$)
26) 4-demethoxy-8-(R)-fluoro-7-(daunosaminyl-ramnosyl)-doxorubicinone and its esters in C—14 (I: R=$R_2$=$R_6$=OH; $R_3$=A; $R_1$=H; $R_5$=NH$_2$)
27) 4-demethoxy-8-(R)-fluoro-7-(2",3",4"-amino-esapiranosyl-fucosyl)-doxorubicinone and its esters in C—14 (I: R=$R_2$=OH; $R_3$=A; $R_1$=$R_5$=H; $R_6$=NH$_2$)
28) 4-demethoxy-8-(R)-fluoro-7-(2",3",4"-trideoxy-4"-amino-esapiranosyl-ramnosyl)-doxorubicinone (I: R=$R_2$=OH; $R_3$=A; $R_1$=$R_5$=H; $R_6$=NH$_2$)
29) 4-demethoxy-8-(R)-fluoro-7-(fucosyl-4'-O-fucosyl)-doxorubicinone and its esters in C—14 (I: R=$R_2$=$R_5$=$R_6$=OH; $R_3$=A; $R_1$=H)
30) 4-demethoxy-8-(R)-fluoro-7-(fucosyl-4'-O-ramnosyl)-doxorubicinone and its esters in C—14 (I: R=$R_2$=$R_5$=$R_6$=OH; $R_3$=A; $R_1$=H)
31) 8-(R)-fluoro-doxorubicin and its esters in C—14 (I: R=$R_3$=OH; $R_1$=OCH$_3$; $R_2$=NH$_2$)
32) 8-(R)-fluoro-3'-deamino-4'deoxy-4'amino-doxorubicin and its esters in C—14 (I: R=OH; $R_1$=OCH$_3$; $R_2$=H; $R_3$=NH$_2$)
33) 8-(R)-fluoro-3'-deamino-4'deoxy-4'-epi-amino-doxorubicin and its esters in C—14 (I: R=OH; $R_1$=OCH$_3$; $R_2$=H; $R_3$=NH$_2$)
34) 8-(R)-fluoro-4'epi-doxorubicin and its esters in C—14 (I: R=$R_3$=OH; $R_1$=OCH$_3$; $R_2$=NH$_2$)
35) 8-(R)-fluoro-7-(daunosaminyl-fucosyl)-doxorubicinone and its esters in C—14 (I: R=$R_2$=$R_6$=OH; $R_1$=OCH$_3$; $R_3$=A; $R_5$=NH$_2$)
36) 8-(R)-fluoro-7-(daunosaminyl-ramnosyl)-doxorubicinone and its esters in C—14 (I: R=$R_2$=$R_6$=OH; $R_3$=A; $R_1$ OCH$_3$; $R_5$=NH$_2$)
37) 8-(R)-fluoro-7-(2",3",4"-trideoxy-4"-amino-esapiranosyl-fucosyl)-doxorubicinone and its esters in C—14 (I: R=$R_2$=OH; $R_1$=OCH$_3$; $R_3$=A; $R_5$=H; $R_6$=NH$_2$)
38) 8-(R)-fluoro-7-(2",3",4"-trideoxy-4"-amino-esapiranosyl-ramnosyl)-doxorubicinone and its esters in C—14 (I: R=$R_2$ OH; $R_1$=OCH$_3$; $R_3$=A; $R_5$=H; $R_6$=NH$_2$)
39) 8-(R)-fluoro-7-(fucosyl-4'-O-fucosyl)-doxorubicinone and its esters in C—14 (I: R=$R_2$=$R_5$=$R_6$=OH; $R_3$=A; $R_1$=OCH$_3$)
40) 8-(R)-fluoro-7-fucosyl-4'-O-ramnosyl)-doxorubicinone and its esters in C—14 (I: R=$R_2$=$R_5$=$R_6$=OH; $R_1$=OCH$_3$; $R_3$=A).

The compounds of formula (I) and their pharmaceutically acceptable salts are prepared by a process comprising the following steps. Condensation between a 8-fluoro-anthracyclinone of formula (II):

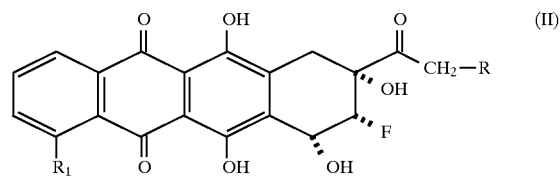

wherein R and $R_1$ are as above defined, and a compound of formula (III)

wherein X is a leaving-group capable of generating, under the condensation conditions, a stable carbocation which can react with an hydroxyl in position C—7 of compound (II). Such leaving-group is suitably chosen among those used in the glycosidation reactions, for example halogen, p-nitrobenzoyloxy-group; $R_7$ is H or a group OH or NH$_2$ suitably protected; $R_8$ is H or OH or NH$_2$ suitably protected or a residue of formula (III'):

wherein $R_9$ and $R_{10}$, same or different, are chosen among H, OH and NH$_2$ suitably protected.

The groups OH are protected as p-nitrobenzoate or allyloxycarbonyl. The groups NH$_2$ are protected as allylcarboxyamide or with trifluoroacetamide.

The symbol ( $\sim$ ) indicates that the substituents $R_7$, $R_8$, $R_9$, $R_{10}$ can be in the axial and/or equatorial configuration. The condensation between compounds (II) and (III) gives the glycoside of formula (IV)

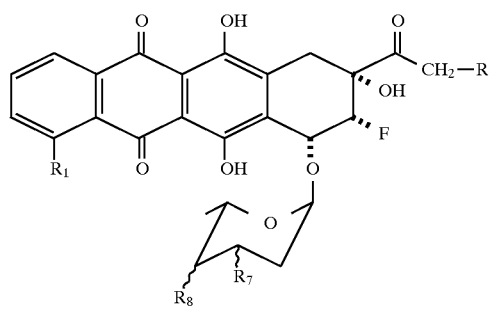

The glycosidation reaction is performed in an organic solvent in the presence of a condensing agent. The condensing agents used are, for example, silver trifluoromethanesulfate, silver perchlorate, mixtures of quicksilver oxide or bromide, boron halogenide, ion-exchanging resin as Amberlite.

Preferably the glycosidation reaction is carried out using an inert organic solvent as benzene, toluene, ethylether, tetrahydrofuran, dioxan, chloroform, methylene chloride or dichloroethane and their mixtures.

The reaction temperature can vary between −40° C. and 40° C., preferably between −20° C. and 20° C., and the time required for the reaction can vary between 5 min and 2 hours.

In the reaction mixture a dehydrator, as activated molecular sieves, can be present.

During the reaction, or at its end, an organic base as pyridine, collidine, triethylamine can be added to the reaction mixture.

The removal of the protecting groups from the groups OH and/or $NH_2$ in the compounds of formula (IV), in order to obtain the wanted compounds of formula (I), can vary according to the protecting group used.

When $R_7$ and/or $R_8$ and/or $R_9$ and/or $R_{10}$, same or different, are a $NH_2$ group protected as trifluoroacetamide and/or a OH group protected as p-nitrobenzoate, the deprotecting reaction is carried out in a polar solvent as water, methanol, ethanol, pyridine, dimethylformamide or their mixtures in the presence of a stoichiometric quantity, or an excess, of an inorganic base as NaOH, KOH, LiOH, $Ba(OH)_2$ and their carbonates. The reaction temperature can vary from 0° C. to 50° C. and the reaction-time can vary from 3 hours and 3 days.

When $R_7$ and/or $R_8$ and/or $R_9$ and/or $R_{10}$, same or different, are a $NH_2$ group protected as allylcarboxyamide and/or a group OH protected as allyloxycarbonate, the deprotection reaction is carried out in an inert solvent and in the presence of a metallic complex as (tetrakis-triphenylphosphine)Pd, as described for example in Tetrahedron Letters, 30 (1989), 3773 or (tetracarbonyl)Ni, as described for example in J.Org.Chem. 38 (1973) 3223.

If preferred the compounds of formula (I) wherein $R_1$, $R_2$ and $R_3$ are as above defined and R is the group OH, can be prepared starting from glycosides of formula (I) or their pharmaceutical acceptable salts where $R_1$, $R_2$ and $R_3$ and the symbol ($\sim$) are as above defined and R is H, by bromination of the carbon atom in position 14 with bromine in chloroform followed by hydrolysis of the so obtained 14-bromo-derivatives with sodium formate at room temperature for 48 hours.

The same product can also be obtained by bromination of the carbon atom in position 14, according to the above described procedure, of the aglycon of formula (II) wherein $R_1$ is as above defined and R is H. This compound, after hydrolysis, which transforms R in the group OH, is glycosylated with a compound of formula (III) as above defined by a glycosidation reaction as above described in order to obtain the wanted product.

If preferred, glycosides of formula (I) can be transformed in the corresponding pharmaceutically acceptable salts, for example hydrochlorides, by treatment with hydrochloric acid in methanol.

Another object of the present application are the 8-fluoro-anthracyclinones of formula (II) wherein the group 8—F and 9—OH are mutually in position cis and wherein R and $R_1$ are as above defined, and their preparation process.

The process is illustrated in the Scheme hereinafter.

The first step is the bromofluorination of an allylalcohol of formula (V), wherein $R_1$ is as above defined, in order to obtain a compound of formula (VI).

The bromofluorination of (V) can be carried out according to various methods, described in literature (ex. Gazz. Chim. It. 121 (1991) 537–545; J.O.C. 58 (1993) 2791–2796), for the bromofluorination of the alkenes.

The second step is the epoxide formation, starting from bromidrine (VI), in order to obtain the compound of formula (VII) wherein $R_1$ is as above defined. This reaction can be carried out using a strong base, according to the known methods described in literature in respect of this kind of reaction.

The third step is the opening of the epoxide in order to obtain the product of formula (VII) wherein $R_1$ is as above defined. Also in this case the reaction methods are described in the literature referring to the opening of an epoxide to give a diol by acid catayisis, preferably mixtures of water, mineral acids and inert organic solvents. The fourth step is the reaction of oxidation of diol (VIII) to the hydroxyketone of formula (IX). The oxidation reaction can be carried out according to known procedures. Preferred are the methods comprising the use of dimethylsulfoxide, as for example the Moffat-oxidation reaction and similar, or of complexes pyridine-chrome, as the chlorochromate of pyridinium.

The last step is the transformation of the fluorohydroxyketone of formula (IX) into the compound of formula (II). This can be carried out according to known methods as the bromination and solvolysis, when necessary with the possible protection of the keto-group (Can. J. Chem. 49 (1971) 2712; J.A.C.S. 98 (1976) 1969; J.A.C.S. 98 (1976) 1967).

The present invention refers also to pharmaceutical compositions containing as active principle an anthracyclinglycoside of formula (I) or a pharmaceutically acceptable salt thereof.

A therapeutically active quantity of a compound according to the present invention (between 2 and 20 mg/m² of body surface, or 0.05–0.5 mg/kg body weight if the product is administered intravenously, or 10–200 mg/m² of body surface or 0.25–5 mg/kg body weight in the case of oral administration) is combined with an inert vector. Conventional vectors can be used and the composition is formulated according to known procedures.

Compositions suitable for intravenous or oral administration are preferred.

The compounds according to the invention are useful in the therapeutical treatment in men and animals. In particular the compounds according to the invention are useful as anti-tumor agents for the administration of therapeutically active quantities of the compound to the patient under treatment.

In particular the compounds showed a surprising activity against a wide number of solid tumors (for example: ovary, breast, lung, uterus tumor) also against those which developed resistance towards the known and normally used anti-tumor agents.

EXAMPLE I 9-(1'-Hydroxyethyl)-7,10-dihydro-6,11-dihydroxy-8-fluoro-9-bromo-5,12-naphthacene-dione ((VI), $R_1$=H).

To a suspension of 9-(1'-hydroxyethyl)-7,10-dihydro-6,11-dihydroxy-5,12-naphthacene dione ((V), $R_1$=H) (9.4 g, 28 mmoles) in methylene chloride (900 ml), a solution of tetrabutylammonium-dihydrogen (18.4 g, at 55%; 33.6 mmoles) in methylene chloride is added under stirring at $-5°$ C., thereafter, always at $-5°$ C. and maintaining the reactor in the darkness, N-bromo-succinimide (6.0 g; 33.6 mmoles) is added. The reaction goes on for 5 hours. Longer reaction time does not increases the yield. A solution of $NaHCO_3$ 10% is added up to neutral pH. The organic phase is dried on $Na_2SO_4$, filtered and evaporated. The residue is purified by flash chromatography using $CHCl_3$ as eluent.

3.6 g (yield 29%) of compound (VI) ($R_1$=H) are obtained.
NMR ($CDCl_3$, δ): 1.45 (3H, d); 3.0–3.5 (2H, q); 3.2–3.4 (2H, q); 3.93 (1H, m); 5.4–5.6 (1H, d); 7.90 (2H, m); 8.30 (2H, m); 13.36 (1H, s); 13.46 (1H, s).

By analogous procedure
4-methoxy-9-(1'-hydroxyethyl)-7,10-dihydro-6,11-dihydroxy-8-fluoro-9-bromo-5,12-naphthacene dione ((VI), $R_1$=$OCH_3$) was obtained.

EXAMPLE II 9-(9-1'-Epoxyethyl)-7,10-dihydro-6,11-dihydroxy-8-fluoro-5,12-napthacene-dione ((VII), $R_1$=H).

A solution of 9-(1'-hydroxyethyl)-7,10-dihydro-6,11-dihydroxy-8-fluoro-9-bromo-5,12-naphthacene-dione (3,6 g, 8,3 mmoles), obtained according to the Example 1, in NaOH 5% (16 ml) is left under stirring for 2 hours at room temperature. The reaction is treated with HCl 1N and the product extracted with $CHCl_3$; the organic phase is dried on $Na_2SO_4$, filtered and evaporated. The obtained residue is purified by flash chromatography using $CHCl_3$ as eluent. 1.6 g (yield 57%) of the title compound are obtained.
NMR ($CDCl_3$, δ): 1.4 (3H, d); 2.62–3.48 (2H, q); 2.9–3.1 (2H, q); 3.26–3.68 (2H, m); 3.10 (1H, m); 4.80–4.96 (1H,d); 7.80 (2H, m); 8.40 (2H, m); 13.35 (1H, s); 14.42 (1H, s).

By analogous procedure:
4-Methoxy-9-(9-1'-epoxyethyl)-7,10-dihydro-6,11-dihydroxy-8-fluoro-5,12-naphthacene-dione ((VII), $R_1$=$OCH_3$)

ESEMPIO III 9-(1'-hydroxyethyl)-7,10-dihydro-6,9,11-trihydroxy-8-fluoro-5,12-naphthacene-dione ((VIII), $R_1$=H).

To a solution of 9-(9-1'-Epoxyethyl)-7,10-dihydro-6,11-dihydroxy-8-fluoro-5,12-naphthacene-dione (1.6 g; 4.7 mmoles), obtained according to example II, in dioxane (700 ml) $H_2O$ (700 ml) is added and thereafter, maintaining the reactor in a bath at 0° C., oleum (700 ml) is slowly dropped therein. At the end of the oleum addition the temperature is left to raise up to room temperature and the solution is stirred for 6 h. A solution of $NaHCO_3$ is added to the mixture up to neutral pH and the product is extracted with $CH_2Cl_2$. The organic phase, dried on $Na_2SO_4$, is evaporated. The title product is obtained (1,7 g; 100% yield).
NMR ($CDCl_3$, δ): 1.40 (3H, d); 2.8–3.1 (2H, q); 3.0–3.3 (2H, q); 4.05 (1H, q); 5.0–5.2 (1H, q); 7.80 (2H,m); 8.30 (2H, m); 13.30 (1H, s); 13.32 (1H, s).

By analogous procedure
4-methoxy-9-(1'-hydroxyethyl)-7,10-dihydro-6,9,11-trihydroxy- 8-fluoro-5,12-naphthacene-dione ((VIII), $R_1$=$OCH_3$).

EXAMPLE IV

9-Acetyl-8(8H)-fluoro-7,10-dihydro-6,9,11-trihydroxy-5,12-naphthacene-dione ((IX), $R_1$=H).

9-(1'-hydroxyethyl)-7,10-dihydro-6,9,11-trihydroxy-8-fluoro-5,12-naphthacene-dione (1.7 g; 4.7 mmoles), prepared according to example III, in anhydrous conditions, is solubilized in DMSO (90 ml), then a mixture of pyridine (1.14 ml; 14.1 mmoles) and trifluoroacetic acid (0.83 ml; 10.8 mmoles) in DMSO (16 ml) is added to the solution. Acetic anhydryde (4.44 ml; 47 mmoles) is added to the mixture and the solution is left under stirring at room temperature for 4 h. Thereafter $H_2O$ is added to the solution, the desired product precipitates.

More product possibly present in the solution is recovered by extraction with $CHCl_3$. The so obtained crude is purified by flash chromatography using $CHCl_3$ as eluent. The title compound is obtained (1.2 g; yield 70%).
NMR ($CDCl_3$, δ): 2.48 (3H, s); 3.18 (2H, s); 3.1–3.6 (2H, m) 3.90 (1H, s); 5.2–5.4 (1H, s); 7.82 (2H, m); 8.38 (2H, m); 13.34 (1H, s); 13.36 (1H, s).

By analogous procedure
4-Methoxy-9-acetyl-8(8H)-fluoro-7,10-dihydro-6,9,11-trihydroxy-5,12-naphthacene-dione ((IX), $R_1$=$OCH_3$) is obtained.

EXAMPLE V

9-Acetyl-8(8H)-fluoro-10-hydro-6,7(7H),9,11-tetrahydroxy-5,12-naphthacene dione (II; $R_1$=H)

In a flask equipped with Dean Stark, to a suspension of 9-acetyl-8(8 H)-fluoro-7,10-dihydro-6,9,11-trihydroxy-5,12-naphthacene-dione (1.2 g; 3.3. mmoles) prepared according to the Example IV, in anhydrous benzene (200 ml), ethylene glycol (5 ml) and a catalytic quantity of p-toluensulphonic acid (60 mg; 0.3 mmoles) are added. The mixture is refluxed at 120° C. for 15 h. The carbonyl-function in position 13 is protected by ketalization. When the reaction is finished the temperature is raised to room temperature and the product precipitates and is collected and washed with water.

The so obtained product is brominated in position 7 with PHPP and AIB in $CCl_4$ by refluxing at 120° C. in $N_2$ current, for 8 hours. The temperature of the rection mixture is raised up to room temperature, the precipitate is filtered and the solution is evaporated. The residue is hydrolized with trifluoroacetic acid (240 ml) and water (60 ml) by refluxing for 1 h.

The temperature is raised at room temperature, then is cooled at 7° C. The product precipitates, is washed with water and dried. It results to be a mixture of epimers in position 7 (a=70%, b=30%). The wanted epimer is isolated by HPLC in order to obtain the title product (312 mg; yield 24%).
NMR ($CDCl_3$, δ): 2.50 (3H, s); 3.1–3.4 (2H, m); 3.85 (1H, d) 4.82 (1H, s); 5.04–5.22 (1H, q); 5.50 (1H, m); 7.85 (2H, m); 8.40 (2H, m); 13.28 (1H, s); 14.54 (1H, s).

By analogous procedure
4-Methoxy-9-acetyl-8(8H)-fluoro-10-hydro-6,7(7H),9,11-tetrahydroxy-5,12-naphthacene dione (II; $R_1$=$OCH_3$)

EXAMPLE VI

Protected 4-demethoxy-8(R)-fluoro-daunorubicin (IV, R=$R_1$=H, $R_7$=$NHCO_2CH_2CH$=$CH_2$, $R_8$=p—CO—$C_6H_4$—$NO_2$).

To a solution of 9-acetyl-8(8H)-fluoro-10-hydro-6,7(7H),9,11-tetrahydroxy-5,12-naphthacene dione (77 mg.; 0.2 mmoles), obtained according to example V and protected daunosamine ((III), X=R$_8$=OCOC$_6$H$_4$NO$_2$; R$_7$=NHCO$_2$CH$_2$CH=CH$_2$) (127 mg; 0.24 mmoles) in anhydrous methylene chloride (40 ml) and anhydrous ethylether (10 ml) molecular sieves 4°A (1,2 g) are added. To this solution, maintained at −10° C. and under anhydrous nitrogen current, trimethyl-silyl-triflate (107 mg; 0.48 mmoles) is added. The reaction is carried out at −10° C. for 30 minutes. The solution is treated with a solution of NaHCO$_3$, the organic phase is extracted, dried on Na$_2$SO$_4$ and evaporated. The so obtained crude is purified by flash chromatography (CHCl+1% iPrOH). 61 mg (yield 40%) of the title compound are obtained.

NMR (CDCl$_3$, δ): 1.2 (3H, d); 2.0 (2H, m); 2.5 (3H, d); 3.1–3.5 (2H,g); 4.2–4.7 (5H, m); 5.0–5.3 (3H, m); 5.4–5.6 (2H, m); 5.8 (1H, s); 5.9 (1H, m); 7.8 (2H, m); 8.3 (6H, m); 13.7 (1H, s); 13.2 (1H,s).

By analogous procedure

Protected 8-(R)-fluoro-daunorubicin ((IV) R=H, R$_1$=OCH$_3$, R$_7$=NHCO$_2$CH$_2$CH=CH$_2$, R$_8$=p—CO—C$_6$H$_4$—NO$_2$) is obtained.

EXAMPLE VII 4-demethoxy-8-(R)-fluoro-daunorubicin hydrochloride ((I) R=R$_1$=H; R$_2$=NH$_2$.HCl, R$_3$=OH).

The product described in example VI, must undergo two deprotections in order to be transformed in the corresponding compound I.

The product obtained in example VI (61 mg; 0.08 mmoles) is suspended in MeOH/H$_2$O and treated with a solution of K$_2$CO$_3$ 0.5 M in order to deprotect the hydroxygroup in 4'.

The obtained product, by treatment with Ph$_3$P, Tetrakis, 2-methyl-butirric acid in CH$_2$Cl$_2$, under anhydrous conditions, in the darkness, at room temperature, gives, by deprotection of the amino-group in 3', the wanted compound (32 mg; 75%).

This product, by treatment with HCl 0.01 N, is salified to title compound.

NMR (CDCl$_3$, δ): 1.3 (3H, d); 2.0–2.2 (2H, m); 2.5 (3H, s); 3.2–3.4 (2H, m); 3.6–3.8 (2H, m); 4.4–4.5 (1H, m); 5.2–5.4 (1H, m); 5.5 (1H, m); 5.7 (1H, m); 8.0 (2H, s); 8.4 (2H, s)

By analogous procedure 8-(R)-fluoro-daunorubicin hydrochloride (I, R=H; R$_1$=OCH$_3$; R$_2$=NH$_2$.HCl, R$_3$=OH).

REACTION SCHEME

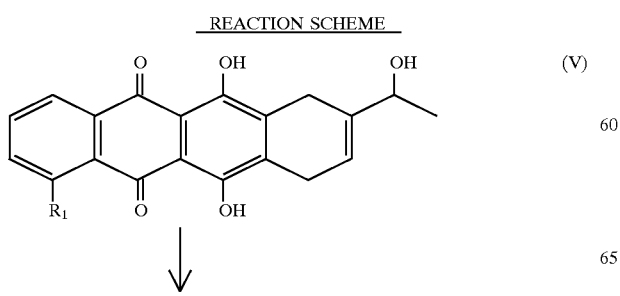

-continued
REACTION SCHEME

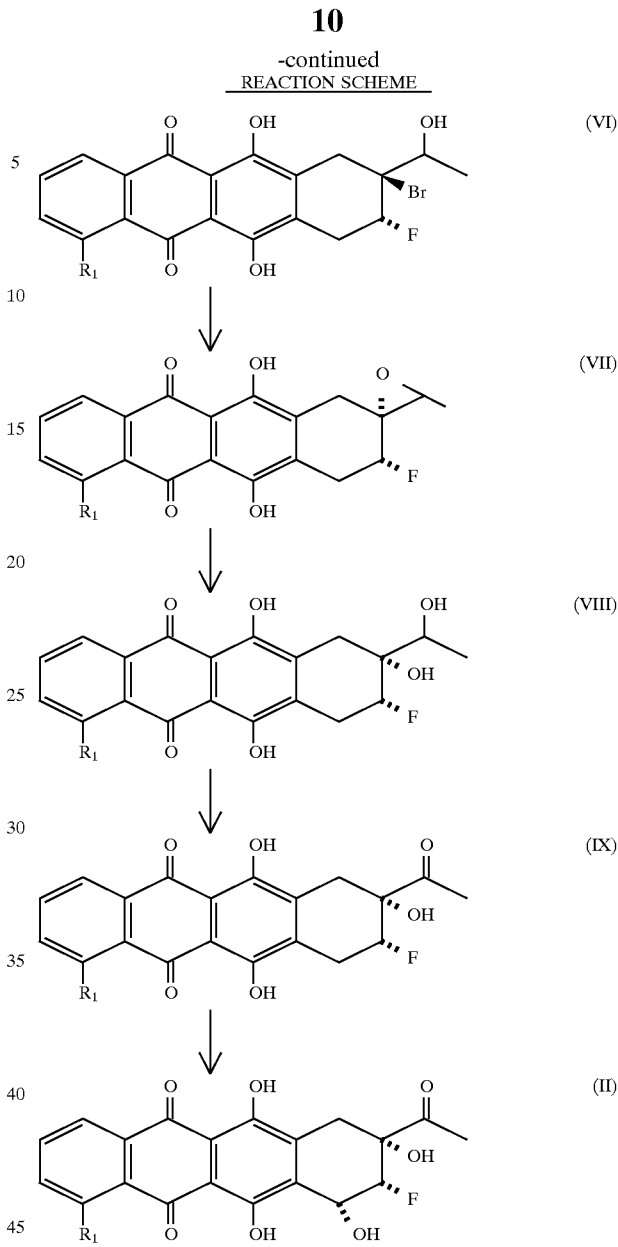

What is claimed is:

1. An 8-(R)-fluoro compound of the formula (I)

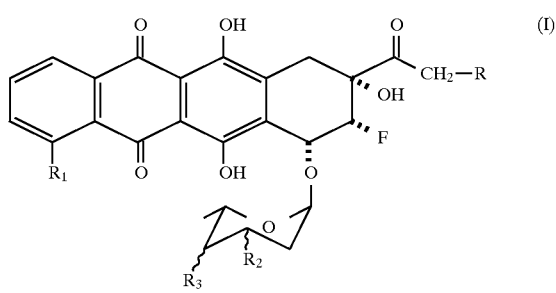

wherein:
R is selected from the group consisting of H, OH, OR$_4$ wherein R$_4$ is chosen in the group consisting of CHO, COCH$_3$, acyl derivative of a carboxylic acid containing up to 6 carbon atoms;

R$_1$ is chosen in the group consisting of: H, OH, OCH$_3$;

R$_2$ is chosen in the group consisting of: H, OH, NH$_2$

R₃ is chosen in the group consisting of: H, OH, NH₂, residue of formula (A)

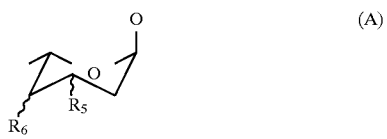

wherein R₅ and R₆, same of different, are chosen in the group consisting of: H, OH, NH₂ and the symbol (∼) indicates that the substituents R₂, R₃, R₅ and R₆ can be in the axial or equatorial configuration;

and wherein the groups 8—F and 9—OH have relative stereochemistry cis or a pharmaceutically acceptable salt.

2. A compound according to claim 1 wherein 8—F and 9—OH have relative stereochemistry cis represented by:
4-demethoxy-8-(R)-fluoro-daunorubicin
4-demethoxy-8-(R)-fluoro-3'-deamino-4'deoxy-4'amino-daunorubicin
4-demethoxy-8-(R)-fluoro-3'-deamino-4'deoxy-4'-epi-amino-daunorubicin
4-demethoxy-8-(R)-fluoro-3'-deamino-4'epi-daunorubicin
4-demethoxy-8-(R)-fluoro-7-(daunosaminyl-fucosyl)-daunorubicinone
4-demethoxy-8-(R)-fluoro-7-(daunosaminyl-ramnosyl)-daunorubicinone
4-demethoxy-8-(R)-fluoro-7-(2",3",4"-trideoxy-4"-amino-esapiranosyl-fucosyl)-daunorubicinone
4-demethoxy-8-(R)-fluoro-7-(2",3",4"-trideoxy-4"-amino-esapiranosyl-ramnosyl)-daunorubicinone
4-demethoxy-8-(R)-fluoro-7-(fucosyl-4'-O-fucosyl)-daunorubicinone
4-demethoxy-8-(R)-fluoro-7-(fucosyl-4'-O-ramnosyl)-daunorubicinone
8-(R)-fluoro-daunorubicin
8-(R)-fluoro-3'-deamino-4'deoxy-4'amino-daunorubicin
8-(R)-fluoro-3'-deamino-4'deoxy-4'-epi-amino-daunorubicin
8-(R)-fluoro-4'epi-daunorubicin  8-(R)-fluoro-7-(daunosaminyl-fucosyl)-daunorubicinone
8-(R)-fluoro-7-(daunosaminyl-ramnosyl)-daunorubicinone
8-(R)-fluoro-7-(2",3",4"-trideoxy-4"-amino-esapiranosyl-fucosyl)-daunorubicinone
8-(R)-fluoro-7-(2",3",4"-trideoxy-4"-amino-esapiranosyl-ramnosyl)-daunorubicinone
8-(R)-fluoro-7-(fucosyl-4'-O-fucosyl)-daunorubicinone
8-(R)-fluoro-7-(fucosyl-4'-O-ramnosyl)-daunorubicinone
4-demethoxy-8-(R)-fluoro-doxorubicin and its esters in C—14
4-demethoxy-8-(R)-fluoro-3'-deamino-4'deoxy-4'amino-doxorubicin and its esters in C—14
4-demethoxy-8-(R)-fluoro-3'-deamino-4'deoxy-4'-epi-amino-doxorubicin and its esters in C—14
4-demethoxy-8-(R)-fluoro-4'epi-doxorubicin and its esters in C—14
4-demethoxy-8-(R)-fluoro-7-(daunosaminyl-fucosyl)-doxorubicinone and its esters in C—14
4-demethoxy-8-(R)-fluoro-7-(daunosaminyl-ramnosyl)-doxorubicinone and its esters in C—14
4-demethoxy-8-(R)-fluoro-7-(2",3",4"-trideoxy-4"-amino-esapiranosyl-fucosyl)-doxorubicinone and its esters in C—14
4-demethoxy-8-(R)-fluoro-7-(2",3",4"-trideoxy-4"-amino-esapiranosyl-ramnosyl)-doxorubicinone and its esters in C—14
4-demethoxy-8-(R)-fluoro-7-(fucosyl-4'-O-fucosyl)-doxorubicinone and its esters in C—14
4-demethoxy-8-(R)-fluoro-7-(fucosyl-4'-O-ramnosyl)-doxorubicinone and its esters in C—14
8-(R)-fluoro-doxorubicin and its esters in C—14
8-(R)-fluoro-3'-deamino-4'deoxy-4'amino-doxorubicin and its esters in C—14
8-(R)-fluoro-3'-deamino-4'deoxy-4'-epi-amino-doxorubicin and its esters in C—14
8-(R)-fluoro-3'-deamino-4'epi-doxorubicin and its esters in C—14
8-(R)-fluoro-7-(daunosaminyl-fucosyl)-doxorubicinone and its esters in C—14
8-(R)-fluoro-7-(daunosaminyl-ramnosyl)-doxorubicinone and its esters in C—14
8-(R)-fluoro-7-(2",3",4"-trideoxy-4"-amino-esapiranosyl-fucosyl)-doxorubicinone and its esters in C—14
8-(R)-fluoro-7-(2",3",4"-trideoxy-4"-amino-esapiranosyl-ramnosyl)-doxorubicinone and its esters in C—14
8-(R)-fluoro-7-(fucosyl-4'-O-fucosyl)-doxorubicinone and its esters in C—14 or
8-(R)-fluoro-7-(fucosyl-4'-O-ramnosyl)-doxorubicinone and its esters in C—14.

3. A compound of formula II

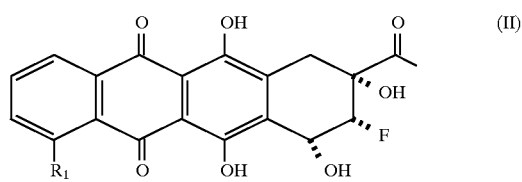

wherein R₁ is defined in claim 1, and the groups 8—F and 9—OH have relative stereochemistry cis.

4. A process for the preparation of a compound of formula (II) according to claim 3 wherein an allylalcohol of formula (V)

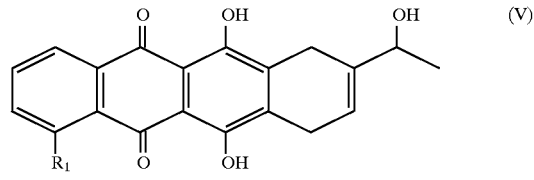

is bromofluorinated to give a compound of formula (VI)

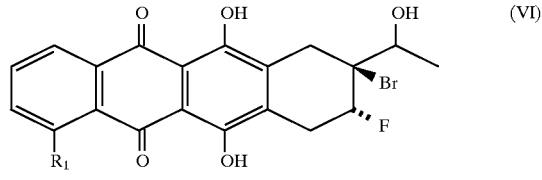

which when treated with a base is transformed into the epoxide of formula (VII)

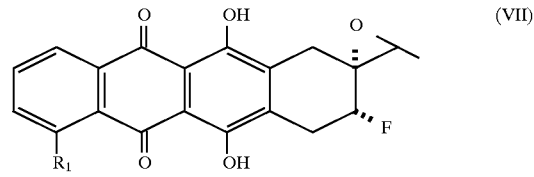

which is transformed, by treatment with acids in aqueous solution, into the corresponding diol of formula (VIII)

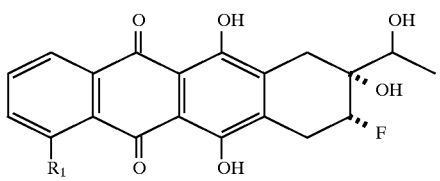 (VIII)

which is oxidized to a fluoro-hydroxy-ketone of formula (IX)

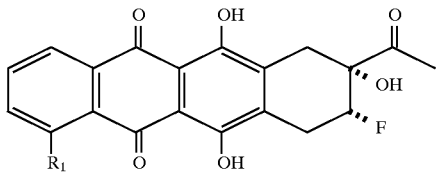 (IX)

which is finally brominated and subjected to solvolysis in position 7 giving the aglycon (II).

5. A pharmaceutical composition for use in treating tumors of the ovary, breast, lung, uterus or colon containing a therapeutically effective amount of a compound of formula (I) according to claim 1, or its pharmaceutically acceptable salt, in combination with a pharmaceutically acceptable vector or diluent.

6. A method for the treatment of tumors of the ovary, breast, lung, uterus or colon wherein an effective amount of a compound of formula (I) according to claim 1 is administered to the patient.

* * * * *